(12) United States Patent
Wong et al.

(10) Patent No.: US 8,361,764 B1
(45) Date of Patent: Jan. 29, 2013

(54) GENES AND ENZYMES FOR DEGRADATION OF FERULIC ACID CROSSLINKS

(75) Inventors: Dominic W. S. Wong, El Cerrito, CA (US); Victor J. Chan, Oakland, CA (US); Meiling Shang, Millbrae, CA (US); Mary J. Zidwick, Wayzata, MN (US); Hans H. Liao, Superior, CO (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 232 days.

(21) Appl. No.: 12/893,922

(22) Filed: Sep. 29, 2010

Related U.S. Application Data

(60) Provisional application No. 61/247,499, filed on Sep. 30, 2009.

(51) Int. Cl.
*C12N 9/18* (2006.01)
*C12P 7/40* (2006.01)
*C12P 7/42* (2006.01)
(52) U.S. Cl. .......................... 435/146; 435/136; 435/197
(58) Field of Classification Search .................. None
See application file for complete search history.

*Primary Examiner* — Rebecca Prouty
(74) *Attorney, Agent, or Firm* — Howard V. Owens; Lesley Shaw; John D. Fado

(57) ABSTRACT

Novel genes that code for a family of feruloyl esterases that break down ferulic acid crosslinks between polysaccharide chains and between polysaccharides and lignins in plant cell walls are described herein as well as a method of rapid gene discovery.

6 Claims, No Drawings

SEQUENCE LISTING

<160> NUMBER OF SEQ ID NOS: 12

<210> SEQ ID NO 1
<211> LENGTH: 228
<212> TYPE: PRT
<213> ORGANISM: Unknown
<220> FEATURE:
<223> OTHER INFORMATION: Bovine Microbial Isolate

<400> SEQUENCE: 1

Met Val Ile Phe Cys His Gly Phe Ser Gly Thr Lys Asp Gly Pro Leu
1               5                   10                  15

Phe Glu Leu Val Ala Asp Thr Leu Gln Ala His Gly Ile Ala Ser Ile
            20                  25                  30

Arg Phe Asp Phe Asn Gly His Gly Glu Ser Glu Gly Glu Phe Lys Asp
        35                  40                  45

Met Thr Val Pro Asn Glu Ile Val Asp Ala Lys Lys Val Val Glu Tyr
    50                  55                  60

Val Arg Asp Leu Lys Tyr Val Ser Ser Leu Ala Ile Ala Gly His Ser
65                  70                  75                  80

Gln Gly Gly Val Val Ala Ala Met Thr Ala Gly Gln Leu Ser Glu Glu
                85                  90                  95

Leu Gly Glu Pro Ala Phe Gln Ala Val Ala Leu Met Ala Pro Ala Ala
            100                 105                 110

Val Leu Arg Asp Asp Ala Ile Arg Gly Ser Thr Met Gly Lys Gln Tyr
        115                 120                 125

Asp Pro Phe Asp Pro Gly Glu Tyr Val Glu Leu Trp Gly Gly Leu Lys
    130                 135                 140

Leu Gly Gly Lys Tyr Ile Arg Thr Ala Phe Thr Leu Pro Ile Tyr Glu
145                 150                 155                 160

Thr Ala Ala Lys Tyr Gln Gly Pro Ala Leu Ile Ile His Gly Thr Ala
                165                 170                 175

Asp Arg Val Val Pro Tyr Thr Tyr Gly Glu Arg Phe His Gln Ile Trp
            180                 185                 190

Pro Lys Ser Gln Leu Val Ile Gln Asp Tyr Phe Asp His Gly Phe Ser
        195                 200                 205

Gln Asn Val Tyr Arg Thr Thr Asp Ile Val Ser Asp Tyr Leu Ile Lys
    210                 215                 220

Gln Leu Thr Gly
225

<210> SEQ ID NO 2
<211> LENGTH: 263
<212> TYPE: PRT
<213> ORGANISM: Unknown
<220> FEATURE:
<223> OTHER INFORMATION: Bovine Microbial Isolate

<400> SEQUENCE: 2

Met Ala Leu Phe Ser Leu Phe Ser Pro Arg Pro Ser Tyr Glu Val Phe
1               5                   10                  15

Gly Ser His Gly Gly Ile Ser Phe Thr Leu Thr Leu Pro Asp Ser Phe
            20                  25                  30

Asp Pro Ser Lys Asp Lys Cys Pro Met Ala Ile Leu Met His Gly Phe
        35                  40                  45

Met Ser Lys Lys Glu Met Tyr Pro Met Pro Ala Ile Ala Lys Ala Leu
    50                  55                  60

```
Ala Lys Ala Gly Ile Ala Ser Ile Arg Phe Asp Phe Asp Ala His Gly
 65                  70                  75                  80

Lys Ser Glu Gly Arg Phe Met Asp Met Thr Ile Ser Ser Glu Ile Ala
                 85                  90                  95

Asp Ala Lys Ala Val Leu Ala Tyr Ala Arg Asn Leu Pro Phe Val Thr
            100                 105                 110

Asp Ile Ala Leu Ile Gly His Ser Gln Gly Gly Val Val Ala Gly Met
        115                 120                 125

Leu Ala Gly Glu Leu Glu Ser Arg Pro Asp Arg Pro Lys Cys Val Val
130                 135                 140

Gln Leu Ala Pro Ala Ala Val Leu Lys Asp Asp Ala Ile Ala Gly Arg
145                 150                 155                 160

Cys Met His Ala Lys Tyr Asp Ala Ser Asn Pro Pro Glu Tyr Val Asn
                165                 170                 175

Val Phe Phe His Lys Leu Gly Arg Ser Phe Ile Leu Glu Ala Gln Lys
            180                 185                 190

Leu Pro Ile Tyr Glu Val Ser Ala Gln Tyr Ser Gly Pro Val Cys Leu
        195                 200                 205

Ile His Gly Asp Lys Asp Lys Ile Val Pro Leu Lys Tyr Ser Glu His
    210                 215                 220

Tyr His Glu Ala Tyr Lys Thr Ser Glu Leu His Val Leu Lys Gly Glu
225                 230                 235                 240

Gly His Leu Leu Asn Gly Asp Lys Thr Arg Leu Ile Glu Thr Val Thr
                245                 250                 255

Thr Phe Leu Asn Arg His Leu
                260

<210> SEQ ID NO 3
<211> LENGTH: 227
<212> TYPE: PRT
<213> ORGANISM: Unknown
<220> FEATURE:
<223> OTHER INFORMATION: Bovine Microbial Isolate

<400> SEQUENCE: 3

Met Val Ile Phe Cys His Gly Phe Thr Gly Arg Lys Asp Gly Pro Met
1               5                   10                  15

Phe Glu Leu Ile Ala Asp Thr Leu Gln Ala His Gly Ile Ala Ser Ile
            20                  25                  30

Arg Phe Asp Phe Asn Gly His Gly Glu Ser Glu Gly Asp Phe Lys Asp
        35                  40                  45

Met Thr Val Pro Asn Glu Ile Glu Asp Ala Lys Lys Val Val Ala Tyr
    50                  55                  60

Val Arg Asp Leu Arg Tyr Val Ser Ser Leu Ala Ile Val Gly His Ser
65                  70                  75                  80

Gln Gly Gly Val Val Ala Ala Met Thr Ala Gly Gln Leu Ser Glu Glu
                85                  90                  95

Leu Gly Arg Pro Ala Phe Lys Ala Val Ala Leu Met Ala Pro Ala Ala
            100                 105                 110

Val Leu Arg Asp Asp Ala Ile Arg Gly Asn Thr Met Gly Lys Gln Tyr
        115                 120                 125

Asp Pro Phe Asp Pro Gly Glu Tyr Val Glu Leu Trp Gly Gly Leu Lys
    130                 135                 140

Leu Gly Gly Gln Tyr Ile Arg Thr Ala Phe Ser Leu Pro Ile Tyr Glu
145                 150                 155                 160
```

```
Thr Ala Val Lys Tyr Gln Gly Pro Ala Leu Ile Ile His Gly Asn Gly
                165                 170                 175

Asp Arg Val Val Pro Tyr Thr Tyr Gly Glu Arg Phe His Gln Ile Trp
            180                 185                 190

Pro Met Ser Glu Leu Val Ile Gln Glu Tyr Phe Asp His Gly Phe Ser
        195                 200                 205

Gln Asn Ile Tyr Arg Thr Thr Asp Ile Val Ser Asp Tyr Leu Ile Lys
    210                 215                 220

Gln Leu Lys
225

<210> SEQ ID NO 4
<211> LENGTH: 240
<212> TYPE: PRT
<213> ORGANISM: Unknown
<220> FEATURE:
<223> OTHER INFORMATION: Bovine Microbial Isolate

<400> SEQUENCE: 4

Val Asn Ile Ser Tyr Thr Ala His Asp Thr Glu Ala Asn Gly Arg Thr
1               5                   10                  15

Tyr Thr Lys Lys Ala Asn Val Tyr Leu Pro Ala Gly Tyr Ser Pro Asp
            20                  25                  30

Lys Lys Tyr Asn Val Leu Tyr Leu Leu His Gly Ile Gly Gly Asn Glu
        35                  40                  45

Asn Glu Trp Gly Met Thr Gly Asn Asn Ser Thr Val Lys Ala Ile Met
    50                  55                  60

Asp Asn Leu Ser Tyr Tyr Gly Asp Ile Asp Ser Phe Ile Val Val Thr
65                  70                  75                  80

Pro Asn Gly Lys Ala Ser Ala Ser Gly Ser Thr Asn Ser Phe Tyr Asn
                85                  90                  95

Phe Gly Ala Glu Leu Arg Tyr Asp Leu Ile Pro Tyr Ile Asp Ser His
            100                 105                 110

Tyr Ser Thr Asn Ala Asp Arg Asp His Arg Ala Ile Ala Gly Leu Ser
        115                 120                 125

Met Gly Gly Met Gln Thr Ile Asn Ile Gly Ile Gly Glu Cys Val Asp
    130                 135                 140

Leu Phe Gly Tyr Phe Gly Ala Phe Ser Ala Ala Pro Thr Ser Asn Ala
145                 150                 155                 160

Ala Ser Lys Thr Ala Ser Leu Leu Asn Gly Asn Ser Tyr Pro Ile His
                165                 170                 175

Tyr Phe Tyr Asn Val Cys Gly Leu Gln Asp Gly Ile Ala Tyr Ser Ser
            180                 185                 190

His Ser Gln Ala Ala Lys Asn Leu Pro Ser Val Cys Asn Gln Phe Val
        195                 200                 205

Asn Gly Gln Asn Tyr Met Trp Gln Glu Leu Asn Gly Gly His Asp Phe
    210                 215                 220

Asn Ile Trp Tyr Leu Gly Phe Tyr Asn Phe Ala Gln Ile Ala Phe Lys
225                 230                 235                 240

<210> SEQ ID NO 5
<211> LENGTH: 314
<212> TYPE: PRT
<213> ORGANISM: Unknown
<220> FEATURE:
<223> OTHER INFORMATION: Bovine Microbial Isolate

<400> SEQUENCE: 5
```

-continued

Met Lys Lys Thr Ile Leu Ser Val Cys Met Cys Leu Ser Ala Val
1               5                   10                  15

Ala Met Ala Gln Pro Ala Gly Gly Phe Gly Phe Gln Ala Pro Gln
            20                  25                  30

Val Lys Leu Glu Thr Ser Gln Glu Trp Lys Asp Val Asn Tyr Ala Gly
            35                  40                  45

Asp Asp Gln Ala Tyr His Thr Cys Asp Ile Tyr Leu Pro Lys Gln Glu
    50                  55                  60

Lys Ala Ser Tyr Pro Val Val Ile His Ile Tyr Gly Ser Ala Trp Phe
65                  70                  75                  80

Ser Asn Asn Ser Lys Gly Met Ala Asp Leu Gly Thr Ile Val Lys Ser
                85                  90                  95

Leu Leu Asp Ala Gly Phe Ala Val Val Cys Pro Asn His Arg Ser Ser
                100                 105                 110

Met Asp Ala Lys Trp Pro Ala Gln Ile His Asp Ile Arg Ala Val Ile
                115                 120                 125

Arg Phe Val Arg Gly Glu Ala Lys Tyr Lys Phe Asp Thr Lys Phe
    130                 135                 140

Ile Ala Thr Ser Gly Phe Ser Ser Gly Gly His Leu Ala Ser Thr Ala
145                 150                 155                 160

Ala Thr Thr Ser Gly Thr Lys Gln Thr Lys Val Gly Thr Val Asp Ile
                165                 170                 175

Asp Leu Glu Gly Asn Val Gly Asn Tyr Leu Asn Glu Ser Ser Ala Val
                180                 185                 190

Asp Ala Ala Cys Asp Trp Ser Gly Pro Ile Asp Leu Thr Ala Met Asp
                195                 200                 205

Cys Gly Glu Ser Met Lys Met Gly Glu Asn Ser Pro Glu Asp Val Leu
210                 215                 220

Leu Asn Ser Lys Leu Ala Lys Glu Pro Asp Lys Tyr Leu Ser Leu Ser
225                 230                 235                 240

Ala Asn Thr Tyr Val Asp Lys Asn Asp Pro Pro Ile Ile Ile Phe His
                245                 250                 255

Gly Glu Lys Asp Asn Val Val Pro Cys Cys Gln Gly Lys Ala Phe Phe
                260                 265                 270

Glu Thr Leu Lys Ala Ala Gly Val Lys Thr Glu Ala Thr Phe Val Pro
            275                 280                 285

Glu Gly Ser His Gly Gly Pro Ala Met Tyr Val Glu Glu Asn Leu Gln
            290                 295                 300

Lys Met Val Asn Phe Leu Lys Ala Leu Leu
305                 310

<210> SEQ ID NO 6
<211> LENGTH: 775
<212> TYPE: PRT
<213> ORGANISM: Unknown
<220> FEATURE:
<223> OTHER INFORMATION: Bovine Microbial Isolate

<400> SEQUENCE: 6

Met Lys Lys Leu Ala Met Ile Ser Met Thr Ala Leu Leu Ala Gly Cys
1               5                   10                  15

Thr Ala Ala Pro Asp Leu Glu Lys Gln Ile Asp Glu Leu Tyr Gln Lys
            20                  25                  30

Met Pro Gln Glu Glu Arg Ile Ala Gln Leu Arg Ser Met Tyr Met Asp
            35                  40                  45

Glu Leu Phe Asp Glu Ala Gly Asn Leu Asp Thr Ala Lys Cys Arg Glu

```
            50                  55                  60
Leu Ile Pro Tyr Gly Ile Gly His Phe Ser Gln Phe Ala Leu Gln Lys
 65                  70                  75                  80

Pro Arg Asp Pro Asn Asp Ile Arg Asp Lys Val Val Ala Val Gln Asp
                 85                  90                  95

Trp Leu Met His Asn Thr Pro Asn Gly Ile Pro Ala Leu Phe His Glu
                100                 105                 110

Glu Val Leu Ser Gly Ile Asn Thr Lys Gly Ser Thr Ile Tyr Pro Gln
                115                 120                 125

Gln Ile Gly Gln Ala Gly Ser Phe Asn Thr Ala Leu Ala Glu Leu Lys
130                 135                 140

Thr Arg Gln Thr Ser Thr Ala Met Arg Lys Met Gly Gly Val Leu Ala
145                 150                 155                 160

Leu Ser Pro Met Val Asp Val Cys Arg Thr Pro Ser Phe Asn Arg Leu
                165                 170                 175

Glu Glu Ser Tyr Gly Glu Asp Ala Tyr Leu Ser Ala Ala Met Gly Val
                180                 185                 190

Ala Phe Val Lys Gly Leu Gln Gln Gly Asp Leu Lys Lys Gly Val Gly
                195                 200                 205

Ala Cys Thr Lys His Tyr Leu Gly Tyr Gly Gly Gly Asp Ala Glu
210                 215                 220

Glu Lys Glu Leu Met Glu Ile Leu Leu Pro His Glu Thr Met Ile
225                 230                 235                 240

Arg Lys Thr Gly Ser Val Ala Val Met Pro Gly Tyr His Asp Val His
                245                 250                 255

Gly Thr Arg Cys Val Cys Asn Ser Glu Ile Leu Gln Asp Ile Leu Arg
                260                 265                 270

Asp Tyr Val Gly Phe Asp Gly Met Val Val Ser Asp Tyr Thr Ala Ile
                275                 280                 285

Asp Gln Ile Pro Gly Leu Asp Ser Val Val Gln Lys Ala Ala Ala Ala
290                 295                 300

Ile Asn Asn Gly Asn Asp Val Asp Phe Pro His Gly Ala Asn Tyr Lys
305                 310                 315                 320

Phe Leu Gln Asp Ala Ile Asp Gln Glu Leu Val Lys Pro Glu Val Leu
                325                 330                 335

Glu Arg Ala Val Lys Asn Val Leu Arg Ile Lys Phe Arg Ala Gly Leu
                340                 345                 350

Phe Asp Lys Asp Ala Tyr Leu Tyr Ser Thr Glu Asn Ile Thr Leu Asp
                355                 360                 365

Thr Pro Glu Glu Arg Gln Thr Ala Tyr Asp Ile Ala Thr Gln Ser Val
370                 375                 380

Val Leu Leu Glu Asn Lys Gly Val Leu Pro Leu Lys Glu Ala Lys Asn
385                 390                 395                 400

Ile Leu Leu Thr Gly Pro Asn Ala Asn Thr Met Trp Ala Met Leu Gly
                405                 410                 415

Asp Tyr Ser Phe Pro Ala Met Ser Tyr Phe Trp Lys Arg Val Gln Asp
                420                 425                 430

Asp Leu Asp His Pro His Thr Ile Thr Leu Leu Glu Gly Met Lys Ala
                435                 440                 445

Lys Ala Pro Glu Gly Val Asn Leu Met Tyr Glu Arg Gly Cys Asp Trp
450                 455                 460

Thr Glu Glu Ile Glu Thr Lys Tyr Gly Glu Leu Gly Asp Ala Arg Ala
465                 470                 475                 480
```

-continued

Trp Glu Tyr Glu Leu Leu His Arg Lys Val Asp Ser Gly Glu Lys Ala
                485                 490                 495

Asp Lys Ala Asn Ala Leu Lys Leu Ala Lys Leu Ala Asp Val Ile Val
            500                 505                 510

Ala Ala Val Gly Glu Asn Val Met Leu Cys Gly Glu Asn Arg Asp Arg
        515                 520                 525

Lys Gly Leu Arg Leu Pro Gly Lys Gln Glu Gln Phe Val Lys Glu Leu
    530                 535                 540

Leu Ala Thr Gly Lys Pro Val Leu Val Met Phe Gly Gly Arg Ala
545                 550                 555                 560

Gln Val Val Ser Gly Leu Ala Glu Gln Cys Ala Ala Val Ile Gln Ala
                565                 570                 575

Trp Tyr Pro Gly Glu Glu Gly Gly Asn Ala Val Ala Asp Ile Leu Tyr
            580                 585                 590

Gly Lys Val Ser Pro Ser Ala Lys Leu Ser Val Ser Tyr Pro Asn Thr
        595                 600                 605

Glu Val Tyr Glu Pro Leu Cys Tyr Asn Cys Gln Ala Glu Lys Asp Pro
    610                 615                 620

Arg Val Gln Trp Pro Phe Gly Tyr Gly Leu Ser Tyr Thr Thr Phe Glu
625                 630                 635                 640

Tyr Gln Asn Leu Lys Val Asp Ser Ala Ala Thr Thr Ala Asp Gln Ser
                645                 650                 655

Ile Asn Leu Ser Phe Glu Val Lys Asn Thr Gly Gln Val Ala Ala Asp
            660                 665                 670

Glu Ile Ala Gln Ile Tyr Leu Ser Pro Thr Ala Asp Asp Gln Asn Ile
        675                 680                 685

Arg Pro Ile Gln Leu Gln Gly Phe Ala Arg Val Ser Leu Asn Pro Gly
    690                 695                 700

Glu Thr Lys Thr Val Lys Val Lys Leu Tyr Thr Glu Gln Phe Gly Phe
705                 710                 715                 720

Tyr Thr Asn Asp Gly Lys Arg Leu Trp Ile Val Arg Pro Gly Ser Phe
                725                 730                 735

Ile Val Lys Val Gly Ala Ser Ser Gln Asp Ile Arg Leu Gln Gln Gln
            740                 745                 750

Val Thr Leu Ser Gly Asn Leu Val Ser Asn Pro Leu Lys Glu Phe Tyr
        755                 760                 765

Phe Ser Lys Thr Ser Ile Glu
    770                 775

<210> SEQ ID NO 7
<211> LENGTH: 277
<212> TYPE: PRT
<213> ORGANISM: Unknown
<220> FEATURE:
<223> OTHER INFORMATION: Bovine Microbial Isolate

<400> SEQUENCE: 7

Met Ala Phe Ile Thr Val Asn Phe Met Ser Glu Ala Leu Met Arg Thr
1               5                   10                  15

Val Thr Val His Val Val Leu Pro Ala Asp Lys Ile Ala Glu Pro Gly
                20                  25                  30

Met Pro Glu Pro Lys His Thr Asp Phe Pro Ala Leu Tyr Leu Leu His
            35                  40                  45

Gly Val Phe Gly Asn Gln Thr Asp Trp Ala Leu Arg Thr Arg Val Gln
        50                  55                  60

Arg Met Ala Glu Asn Ser Asp Leu Ala Leu Ile Met Pro Ala Gly Glu

-continued

```
                65                  70                  75                  80
Asn Ala Phe Tyr Leu Asp Gln Glu Ala Thr His Ala Asn Tyr Gly Asp
                    85                  90                  95
Phe Val Gly Arg Glu Leu Pro Glu Ile Met Arg Arg Met Phe Pro Leu
                    100                 105                 110
Ser Pro Arg Arg Glu Asp Cys Phe Ile Ala Gly Leu Ser Met Gly Gly
                    115                 120                 125
Tyr Gly Ala Leu Arg Asn Gly Leu Lys Tyr His Glu Thr Phe Ser Arg
                    130                 135                 140
Ile Gly Ala Phe Ser Ala Leu Val Leu Asp Gly Ile Glu Asn Arg
145                 150                 155                 160
Thr Asn Asp Ser Pro Leu Phe Ile Glu Arg Arg Asp Tyr Ala Glu Ala
                    165                 170                 175
Ile Phe Gly Pro Leu Asp Lys Val Ala Glu Ser Asp Ile Asn Pro Leu
                    180                 185                 190
Trp Ile Ala Arg Arg Leu Val Glu Ser Gly Thr Glu Leu Pro Gly Leu
                    195                 200                 205
Tyr Leu Ala Cys Gly Thr Glu Asp Phe Leu Phe Glu Pro Asn Val Arg
                    210                 215                 220
Phe Arg Asp Glu Val Arg Lys Leu Gly Cys Glu Leu Thr Trp Asp Glu
225                 230                 235                 240
Gly Pro Tyr Gly His Glu Trp Asp Phe Trp Asn Leu Gln Val Glu Lys
                    245                 250                 255
Phe Ile Asp Trp Leu Pro Leu Ser Glu Ser Gly Thr Gly Ile Asp Ser
                    260                 265                 270
Gly Asn Val Gly Ile
            275
```

<210> SEQ ID NO 8
<211> LENGTH: 453
<212> TYPE: PRT
<213> ORGANISM: Unknown
<220> FEATURE:
<223> OTHER INFORMATION: Bovine Microbial Isolate

<400> SEQUENCE: 8

```
Met Lys Arg Lys Asn His Ile Ser Leu Ala Met Ala Phe Leu Ala Ile
1               5                   10                  15
Gly Leu Met Gly Thr Thr Val Ala Lys Ala Gln Ser Ala Gln Pro Asp
                20                  25                  30
Phe Asp Asp Lys Tyr Ala Thr Glu Met Val Lys Ala Gly Thr Thr Ala
                35                  40                  45
Pro Asp Phe Lys Met Lys Thr Pro Asp Gly Lys Thr Ile Gln Leu Ser
                50                  55                  60
Lys Tyr Ile Lys Ala Arg Pro Lys Asp Lys Gly Lys Thr Val Val Leu
65                  70                  75                  80
Asp Phe Trp Ala Ser Trp Cys Pro Asp Cys Arg Lys Asp Ala Pro Glu
                85                  90                  95
Val Val Arg Leu Tyr Glu Lys Tyr Arg Pro Tyr Gly Ile Glu Phe Ile
                100                 105                 110
Gly Ile Ser Met Asp Thr Asp Val Glu Ala Trp Lys Lys Ala Ile Glu
                115                 120                 125
Gln Tyr Gly Ile Thr Tyr Pro Gln Val Ser Glu Leu Lys Lys Phe Lys
                130                 135                 140
Glu Thr Asp Ile Ala Lys Ala Tyr Gly Val Lys Trp Ile Pro Ser Met
145                 150                 155                 160
```

Val Val Val Gly Pro Asp Gly Glu Val Lys Leu Ser Thr Val Leu Thr
                165                 170                 175

Tyr Lys Val Asp Lys Tyr Leu Lys Glu Leu Thr Thr Gly Lys Tyr Ala
            180                 185                 190

Gly Pro Gly Lys Gly Glu Ala Val Phe Ile Asp Gly Asp His Gly Arg
        195                 200                 205

Leu Lys Ala Ile Ile Gln Lys Pro Leu Gln Gln Gly Glu Lys Cys
    210                 215                 220

Pro Met Val Ile Phe Cys His Gly Phe Ser Gly Arg Lys Asp Gly Pro
225                 230                 235                 240

Met Phe Glu Leu Ile Ala Asp Thr Leu Gln Ala His Gly Ile Ala Ser
                245                 250                 255

Ile Arg Phe Asp Phe Asn Gly His Gly Glu Ser Glu Gly Glu Phe Lys
            260                 265                 270

Asp Met Thr Val Pro Asn Glu Ile Glu Asp Ala Lys Lys Val Val Glu
        275                 280                 285

Tyr Val Arg Asp Leu Arg Tyr Val Ser Ser Leu Ala Ile Val Gly His
    290                 295                 300

Ser Gln Gly Gly Val Val Ala Ala Met Thr Ala Gly Gln Leu Ser Glu
305                 310                 315                 320

Ala Leu Gly Glu Pro Ala Phe Lys Ala Val Ala Leu Met Ala Pro Ala
                325                 330                 335

Ala Val Leu Arg Asp Asp Ala Ile Arg Gly Asn Thr Met Gly Lys Gln
            340                 345                 350

Tyr Asp Pro Phe Asp Pro Gly Glu Tyr Val Glu Leu Trp Gly Gly Leu
        355                 360                 365

Lys Leu Gly Gly Lys Tyr Ile Arg Thr Ala Phe Ser Leu Pro Ile Tyr
    370                 375                 380

Glu Thr Ala Ala Lys Tyr Gln Gly Pro Ala Leu Val Ile His Gly Asn
385                 390                 395                 400

Ala Asp Arg Val Val Pro Tyr Thr Tyr Gly Glu Arg Phe His Gln Ile
                405                 410                 415

Trp Pro Asn Ser Glu Leu Val Ile Gln Glu Tyr Phe Asp His Gly Phe
            420                 425                 430

Ser Gln Asn Leu Tyr Arg Thr Thr Asp Ile Val Ser Glu Tyr Leu Ile
        435                 440                 445

Lys Gln Leu Lys Lys
    450

<210> SEQ ID NO 9
<211> LENGTH: 260
<212> TYPE: PRT
<213> ORGANISM: Unknown
<220> FEATURE:
<223> OTHER INFORMATION: Bovine Microbial Isolate

<400> SEQUENCE: 9

Gly Lys Gly Glu Thr Val Phe Ile Asp Gly Asp Leu Gly Arg Leu Lys
1               5                   10                  15

Ala Leu Ile Gln Lys Pro Ala Leu Gln Gln Gly Glu Lys Cys Pro Met
            20                  25                  30

Val Ile Phe Cys His Gly Phe Ser Gly Thr Lys Asp Gly Pro Leu Phe
        35                  40                  45

Glu Leu Val Ala Asp Thr Leu Gln Ala His Gly Ile Ala Ser Ile Arg
    50                  55                  60

-continued

Phe Asp Phe Asn Gly His Gly Glu Ser Glu Gly Glu Phe Lys Asp Met
65                  70                  75                  80

Thr Val Pro Asn Glu Ile Glu Asp Ala Lys Lys Val Val Glu Tyr Val
                85                  90                  95

Ser Asp Leu Arg Tyr Val Ser Ser Leu Ala Ile Val Gly His Ser Gln
            100                 105                 110

Gly Gly Val Val Ala Ala Met Thr Ala Gly Gln Leu Ser Glu Glu Leu
        115                 120                 125

Gly Glu Ser Pro Phe Lys Ala Val Leu Met Ala Pro Ala Ala Val
130                 135                 140

Leu Arg Asp Asp Ala Ile Arg Gly Ser Thr Met Gly Lys Gln Tyr Asp
145                 150                 155                 160

Pro Phe Asp Pro Gly Glu Tyr Val Glu Leu Trp Gly Gly Leu Lys Leu
                165                 170                 175

Gly Gly Gln Tyr Ile Arg Thr Ala Phe Ser Leu Pro Ile Tyr Glu Thr
            180                 185                 190

Ala Ala Lys Tyr Gln Gly Pro Ala Leu Val Ile His Gly Asn Ala Asp
        195                 200                 205

Arg Val Val Pro Tyr Thr Tyr Gly Glu Arg Phe His Gln Ile Trp Pro
210                 215                 220

Lys Ser Glu Leu Val Ile Gln Glu Tyr Phe Asp His Gly Phe Ser Gln
225                 230                 235                 240

Asn Ile Tyr Arg Thr Thr Asp Ile Val Ser Glu Tyr Leu Ile Lys Gln
                245                 250                 255

Leu Lys Ser Lys
            260

<210> SEQ ID NO 10
<211> LENGTH: 367
<212> TYPE: PRT
<213> ORGANISM: Unknown
<220> FEATURE:
<223> OTHER INFORMATION: Bovine Microbial Isolate

<400> SEQUENCE: 10

Met Gly Ala Arg Val Asn Ala Val Met Asp Glu Ala Val Ser Gly Asn
1               5                   10                  15

Lys Ile Val Gly Ala Glu Leu Ile Val Tyr Arg His Gly Asp Leu Val
                20                  25                  30

Leu Arg Arg Thr Ala Gly His Phe Asp Arg Glu Ala Gly Thr Pro Met
            35                  40                  45

Ile Glu Asn Ala Ile Tyr Arg Leu Ala Ser Val Thr Lys Pro Ile Val
        50                  55                  60

Ala Ala Thr Ala Leu Ala Met Ile Asp Lys Gly Leu Leu Arg Leu Asp
65                  70                  75                  80

Asp Leu Val Ser Asp His Leu Asp Tyr Phe Ala Pro Leu Leu Asp Asp
                85                  90                  95

Gly Ser Pro Ala Pro Ile Thr Ile His His Leu Leu Thr His Thr Ala
            100                 105                 110

Gly Leu Ala Tyr Gly Tyr Asp Asp Glu Ala Ile Ser Thr Gly Leu Gly
        115                 120                 125

Pro Thr Asp Asn Asp Phe Arg Ser Asn Phe Thr Arg Ile Ala Lys Ala
    130                 135                 140

Pro Leu Leu Phe Ala Pro Gly Ser Gly Trp Asn Tyr Ser Val Ala Ile
145                 150                 155                 160

Asp Val Leu Gly Ala Val Leu Ala Ala Val His Gly Gly Ser Leu Gln

```
              165                 170                 175
Asp Ala Val His Ala His Ile Thr Gly Pro Leu Gly Met Asp Glu Thr
            180                 185                 190

Gly Phe Phe Val Ala Asp Leu Ala Arg Leu Ala Lys Pro Tyr Ala Asp
            195                 200                 205

Gly Ala Pro Glu Pro Thr Ala Met Thr Asp Pro Gln Ser Val Ile Gly
            210                 215                 220

Glu Asp Gly Gly Ser Val Val Phe Ser Pro Ser Arg Ile Phe Ser Asp
225                 230                 235                 240

Lys Ala Phe Gln Ser Gly Ala Gly Met Ala Gly Thr Pro Glu Asn
                245                 250                 255

Ile Ala Lys Phe Leu Glu Thr Leu Arg Gln Gly Gly Ser Val Leu
            260                 265                 270

Arg Pro Asp Thr Val Ala Leu Ala Phe Ser Asn Arg Ile Gly Asp Leu
            275                 280                 285

Tyr Arg Gln Asp Gln Gly Gln Arg Phe Gly Tyr Phe Gly Ala Val Ile
            290                 295                 300

Asp Asp Pro Val Ala Ala Glu Ser Pro Ser Gly Ala Gly Thr Val Asn
305                 310                 315                 320

Trp Gly Gly Val Tyr Gly His Ser Trp Leu Val Asp Pro Thr Asn Ala
                325                 330                 335

Ile Thr Ile Val Ser Met Ser Asn Thr Ala Leu Glu Gly Cys Thr Gly
                340                 345                 350

Arg Tyr Pro Lys Asp Leu Ile Arg Ala Val Tyr Asp Asp Leu Ser
            355                 360                 365

<210> SEQ ID NO 11
<211> LENGTH: 313
<212> TYPE: PRT
<213> ORGANISM: Unknown
<220> FEATURE:
<223> OTHER INFORMATION: Bovine Microbial Isolate

<400> SEQUENCE: 11

Met Thr Thr Leu Leu Ile Leu Leu Ala Leu Ala Leu Ile Ala
1               5                   10                  15

Ala Ala Ala Trp Leu Phe Thr Val Arg Thr Val Arg Lys Val Glu Ala
                20                  25                  30

Phe Leu Pro Pro Gln Gly Arg Phe Val Glu Val Pro Gly Ala Arg Leu
            35                  40                  45

His Ile Val Glu Lys Gly Glu Gly Arg Pro Leu Leu Ile His Gly
            50                  55                  60

Leu Ala Gly Val Leu Asn His Phe Thr Tyr Gly Met Val Asp Glu Leu
65                  70                  75                  80

Ala Lys His Tyr Arg Val Ile Ala Val Asp Arg Pro Gly Ser Gly Tyr
                85                  90                  95

Ser Val Arg Gly Ala Gly Ala Ser Ala Asn Leu Phe Asp Gln Ala Asp
            100                 105                 110

Val Met Ala Ala Leu Ile Asp Asn Leu Lys Leu Asp Arg Pro Val Val
        115                 120                 125

Val Gly His Ser Leu Gly Gly Ala Val Ser Leu Ala Leu Ala Gln Arg
        130                 135                 140

His Pro Gln Lys Val Ala Ala Leu Ala Leu Ile Ala Pro Leu Thr His
145                 150                 155                 160

Lys Pro Ala Arg Ile Ser Pro Ala Phe Asp Gly Leu Lys Ile Pro Ser
                165                 170                 175
```

```
Asn Trp Leu Arg His Ala Leu Ala Trp Thr Leu Ala Val Pro Val Gly
            180                 185                 190
Leu Ile Lys Arg Asp Glu Ile Leu Ala Ile Val Phe Gly Pro Glu Pro
        195                 200                 205
Val Leu Glu Asp Phe Gly Thr Gln Gly Gly Gly Leu Leu Gly Val Arg
    210                 215                 220
Pro Ser His Phe Ile Ala Ala Cys Ala Asp Met Asn Ser Glu Leu Ala
225                 230                 235                 240
Gln Leu Leu Asp Met Glu Lys Arg Tyr Pro Ala Met Gln Leu Pro Val
                245                 250                 255
Gly Val Phe Phe Gly Arg Gly Asp Leu Ile Leu Asp Tyr Arg Glu Gln
            260                 265                 270
Gly Glu Ala Leu Ala Ser Lys Val Pro Gly Ala Glu Leu Leu Leu Val
        275                 280                 285
Asp Gly Gly His Met Leu Pro Leu Thr Met Val Gln Lys Ser Ala Asp
    290                 295                 300
Phe Val Arg Gly Val Val Ala Arg Ala
305                 310

<210> SEQ ID NO 12
<211> LENGTH: 306
<212> TYPE: PRT
<213> ORGANISM: Unknown
<220> FEATURE:
<223> OTHER INFORMATION: Bovine Microbial Isolate

<400> SEQUENCE: 12

Met Pro Ile Pro Asp Met Ala Glu Phe Phe Thr Leu Ala His Phe Ser
1               5                   10                  15
Asp Val His Leu Pro Pro Val Phe Gly Ser Gly Trp Arg His Trp Asn
            20                  25                  30
Ala Lys Arg Ala Leu Gly Tyr Met Asn Trp Leu Arg Lys Arg Arg Arg
        35                  40                  45
Val His His Gly Glu Val Ala Asp Lys Leu Leu Ala Asp Ala Ala Ala
    50                  55                  60
Leu Arg Val Asp His Ile Ala Ile Thr Gly Asp Leu Ile Asn Leu Gly
65                  70                  75                  80
Leu Pro Ser Glu Tyr Glu Ala Ala His Ala Trp Leu Gln Ser Ile Gly
                85                  90                  95
Ser Pro Gly Asp Val Thr Val Val Pro Gly Asn His Asp Ile Tyr Ser
            100                 105                 110
Ser Leu His Gly Asp Pro Gly Val Ala Arg Trp Ala Glu Tyr Met Gly
        115                 120                 125
Gly Glu Asn Asp Thr Leu Ala Phe Pro Phe Val Arg Arg Val Gly Pro
    130                 135                 140
Ile Ala Val Val Gly Leu Asn Ser Ala Val Glu Thr Pro Pro Phe Ile
145                 150                 155                 160
Ala Ser Gly Arg Leu Gly Ala His Gln Leu Glu Ile Ala Gly Glu Gln
                165                 170                 175
Leu Glu Ala Leu Gly Glu Lys Gly Ile Ala Arg Val Val Met Ile His
            180                 185                 190
His Pro Pro Leu Pro Asp Leu Ala Pro Pro Arg Arg Ala Leu Ser Asp
        195                 200                 205
Ala Ala His Phe Ala His Leu Leu Glu Arg Gly Asn Ala Glu Leu Val
    210                 215                 220
```

-continued

```
Ile Tyr Gly His Asn His Gln Ser Arg Val Asp Trp Leu Pro Ser Arg
225             230                 235                 240

Thr Lys Pro Ile Pro Val Val Gly Val Ala Ser Ala Ser Ala Gly Val
            245             250                 255

Thr His Gly Asp Glu Pro Leu Ala Ser Tyr Asn Leu Phe Thr Phe Phe
            260             265             270

Lys Ser Asp Ser Gly Leu Arg Ile Arg His Val Val Arg Gly Ile Asp
        275             280                 285

Ala Pro Asn Ser Pro Val Arg Lys Ile Ser Glu Ala Val Leu Thr Pro
    290             295             300

Pro Pro
305
```

GENES AND ENZYMES FOR DEGRADATION OF FERULIC ACID CROSSLINKS

RELATED APPLICATIONS

This application is claims priority to U.S. Provisional Patent Application Ser. No. 61/247,499, filed Sep. 30, 2009 the contents of which are incorporated herein by reference in their entirety.

FIELD OF THE INVENTION

The invention relates to novel genes that code for a family of feruloyl esterases that break down ferulic acid crosslinks between polysaccharide chains and between polysaccharides and lignins in plant cell walls and a rapid method of gene discovery.

BACKGROUND OF THE INVENTION

Ferulic acid is an important component of plant material, forming crosslinks between polysaccharide chains and between polysaccharides and lignin, thus providing structural rigidity to cell walls. Ferulic acid is a cinnamic acid with the chemical name (3-methoxy-4-hydroxy)-3-phenyl-2-propenoic acid, or 3-methoxy-4-hydroxy-cinnamic acid. In the plant cell wall, ferulic acid is bonded via an ester linkage to hydroxyls on sugars, usually arabinose moieties in arabinoxylans or galactose residues in pectins. Ferulic acid dimers and trimers formed by linkages between the phenolic groups provide covalent crosslinks among cellulose, arabinoxylan, xyloglucan, pectin, lignin, as well as protein. The amount of dimers account for 0.14% and 2.5% w/w of the enzyme digest of sugar-beet pulp and corn bran, respectively, suggesting a high degree of crosslinking in the bran cell wall of corn. It has been calculated that each heteroxylan macromolecule contains ~75 esterified ferulic acid groups and ~30 diferulic bridges. These crosslinks limit carbohydrate bioavailability, resulting in lower conversion of the plant material into useful products or nutrients. To overcome this limitation, the ester bonds are hydrolyzed by feruloyl esterases, which are produced by numerous microorganisms that utilize complex plant material as nutrients. Feruloly esterases (FAE, E.C. 3.1.1.73) (ferulic acid esterases, cinnamoyl esterases, cinnamic acid hydrolases, p-coumaroyl esterases, hydroxycinnamoyl esterases, etc.) belong to a subclass of carboxylic esterases (E.C. 3.1.1). The enzyme cleaves ester bonds between hydroxycinnamic acids esterified to arabinoxylans and certain pectins present in plant cell walls.

Feruloly esterase forms a part of the enzyme complexes that are elaborated by fungi or bacteria that metabolize plant materials. FAE plays a key role in enhancing the accessibility of other biomass-degrading enzymes, and subsequent hydrolysis of plant fibers by removing the ferulic acid side chains and crosslinks. This enzyme reaction may well be an important controlling factor for increasing the extent of degradation of lignocellulosic biomass for bioenergy conversion, and pulp and paper manufacture. In biomass degradation, FAE is an integral part of an enzyme system that acts collectively and synergistically with a variety of other cellulolytic and xylanolytic enzymes to enhance biomass degradation. This in turn increases the yield of hexose and pentose sugars in the bioconversion as feedstock for yeast fermentation to biofuel or other value-added chemicals. The enzyme also aids in solubilizing lignin-polysaccharide complexes in paper pulp processing. The enzyme together with a number of glycanases and oxidases, have been implicated in the improvement of bread-making quality and related cereal processing. The importance of FAE also relates to the enzyme product, ferulic acid and feruloylated oligosaccharides, which have potential applications for food and medicinal uses. Ferulic acid and its derivatives are strong antioxidants, and have gel-forming properties. The biotransformation of ferulic acid to vanillin has been extensively investigated. The antioxidative and gelling effects have been utilized to form potential protective agents against photooxidative skin damage and for wound management.

The use of feruloyl esterases for biomass degradation and conversion has been severely hampered by the fact that there are very few known existing gene sequences and enzymes, due to the lack of workable, effective, high-throughput method for direct gene discovery of this group of enzymes. An expanded diverse pool of feruloyl esterase genes/enzymes would enable fine control over processing of complex and variable biomass materials. The immediate impact of the development is to increase the extent of degradation of lignocellulosic biomass for bioenergy conversion as well as for food and medicinal uses.

Technologies enabling rapid discovery of new genes, new enzymes, new reactions and processes are key to continuous growth in the use of biocatalytic processes in many industries. Increasing the number of enzymatic candidates feasible for increasing the commercial viability of biomass conversion is key for the fuel ethanol industry and would equally benefit other industries, such as pharmaceuticals, diagnostics, cosmetic, food and beverages and other sectors employing biocatalysis as a technology platform. A method enabling rapid discovery and isolation of more efficient biocatalytic genes is therefore desired.

SUMMARY OF THE INVENTION

An embodiment of the invention is novel ferulic acid esterase genes. Another embodiment is the ferulic acid esteases coded for by these genes. Cloning of these new genes in recombinant hosts provides a wide selection of feruloyl esterases with biochemical properties uniquely tailored for target applications.

A further embodiment is the use of these esterases in the degradation of biomass or plant matter from various waste or processing streams, including but not limited to agricultural food and animal feed processing, paper processing; wherein the phenolic by products of this processing finds further application as products in food, medicine and biofuel.

A further embodiment is a novel method for rapid direct gene discovery that includes the formulation and use of a substrate gel assay plate, and an enrichment process by serial dilutions progressive to isolate the target gene from DNA libraries constructed from individual organisms or collections of organisms.

DESCRIPTION OF THE INVENTION

The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. Any numerical values, however, inherently contain certain errors necessarily resulting from error found in their respective measurement.

It will be understood by those skilled in the art that the terms "ferulic acid esterase" or "feruloyl esterase" as described herein refers to those esterases containing nucleic acid sequences synonymous with the exemplified coding sequences of SEQ ID NO's 1-12. Nucleic acid sequences are synonymous if the amino acid sequences encoded by those nucleic acid sequences are the same. The degeneracy of the genetic code is well known to the art. For many amino acids, there is more than one nucleotide triplet which serves as the codon for a particular amino acid, and one of ordinary skill in the art understands nucleotide or codon substitutions which do not affect the amino acid(s) encoded. It is further understood in the art that codon substitutions to conform to common codon usage in a particular recombinant host cell is sometimes desirable.

A total of 12 FAE genes have been isolated, sequenced, and cloned, represented by SEQ ID NO.'s 1-12. The primary structures are presented in FIG. 1. A BLAST of public databanks shows highest bit score in a range from 32 to 48% identity. In the case of C1, C2, C3, C8, C9, and C10 the top hit scores refer to hydrolases of α/β family. C4 is most similar (41% identical) to the fungal *Orpinomyces* sp. PC-2 FAE. The rest of the clones have hit scores referring to esterases of some type. All taken together, these 12 FAE genes are novel.

TABLE 1

THE PRIMARY STRUCTURES OF C1 TO C12

| | |
|---|---|
| C1 (SEQ ID NO: 1) | MVIFCHGFSG TKDGPLFELV ADTLQAHGIA SIRFDFNGHG ESEGEFKDMT VPNEIVDAKK VVEYVRDLKY VSSLAIAGHS QGGVVAAMTA GQLSEELGEP AFQAVALMAP AAVLRDDAIR GSTMGKQYDP FDPGEYVELW GGLKLGGKYI RTAFTLPIYE TAAKYQGPAL IIHGTADRVV PYTYGERFHQ IWPKSQLVIQ DYFDHGFSQN VYRTTDIVSD YLIKQLTG |
| C2 (SEQ ID NO: 2) | MALFSLFSPR PSYEVFGSHG GISFTLTLPD SFDPSKDKCP MAILMHGFMS KKEMYPMPAI AKALAKAGIA SIRFDFDAHG KSEGRFMDMT ISSEIADAKA VLAYARNLPF VTDIALIGHS QGGVVAGMLA GELESRPDRP KCVVQLAPAA VLKDDAIAGR CMHAKYDASN PPEYVNVFFH KLGRSFILEA QKLPIYEVSA QYSGPVCLIH GDKDKIVPLK YSEHYHEAYK TSELHVLKGE GHLLNGDKTR LIETVTTFLN RHL |
| C3 (SEQ ID NO: 3) | MVIFCHGFTG RKDGPMFELI ADTLQAHGIA SIRFDFNGHG ESEGDFKDMT VPNEIEDAKK VVAYVRDLRY VSSLAIVGHS QGGVVAAMTA GQLSEELGRP AFKAVALMAP AAVLRDDAIR GNTMGKQYDP FDPGEYVELW GGLKLGGQYI RTAFSLPIYE TAVKYQGPAL IIHGNGDRVV PYTYGERFHQ IWPMSELVIQ EYFDHGFSQN IYRTTDIVSD YLIKQLK |
| C4 (SEQ ID NO: 4) | VNISYTAHDT EANGRTYTKK ANVYLPAGYS PDKKYNVLYL LHGIGGNENE WGMTGNNSTV KAIMDNLSYY GDIDSFIVVT PNGKASASGS TNSFYNFGAE LRYDLIPYID SHYSTNADRD HRAIAGLSMG GMQTINIGIG ECVDLFGYFG AFSAAPTSNA ASKTASLLNG NSYPIHYFYN VCGLQDGIAY SSHSQAAKNL PSVCNQFVNG QNYMWQELNG GHDFNIWYLG FYNFAQIAFK |
| C5 (SEQ ID NO: 5) | MKKTILSVCM CCLSAVAMAQ PAGGFGGFQA PQVKLETSQE WKDVNYAGDD QAYHTCDIYL PKQEKASYPV VIHIYGSAWF SNNSKGMADL GTIVKSLLDA GFAVVCPNHR SSMDAKWPAQ IHDIRAVIRF VRGEAKKYKF DTKFIATSGF SSGGHLASTA ATTSGTKQTK VGTVDIDLEG NVGNYLNESS AVDAACDWSG PIDLTAMDCG ESMKMGENSP EDVLLNSKLA KEPDKYLSLS ANTYVDKNDP PIIIFHGEKD NVVPCCQGKA FFETLKAAGV KTEATFVPEG SHGGPAMYVE ENLQKMVNFL KALL |
| C6 (SEQ ID NO: 6) | MKKLAMISMT ALLAGCTAAP DLEKQIDELY QKMPQEERIA QLRSMYMDEL FDEAGNLDTA KCRELIPYGI GHFSQFALQK PRDPNDIRDK VVAVQDWLMH NTPNGIPALF HEEVLSGINT KGSTIYPQQI GQAGSFNTAL AELKTRQTST AMRKMGGVLA LSPMVDVCRT PSFNRLEESY GEDAYLSAAM GVAFVKGLQQ GDLKKGVGAC TKHYLGYGGG GDAEEKELME EILLPHETMI RKTGSVAVMP GYHDVHGTRC VCNSEILQDI LRDYVGFDGM VVSDYTAIDQ IPGLDSVVQK AAAAINNGND VDFPHGANYK FLQDAIDQEL VKPEVLERAV KNVLRIKFRA GLFDKDAYLY STENITLDTP EERQTAYDIA TQSVVLLENK GVLPLKEAKN ILLTGPNANT MWAMLGDYSF PAMSYFWKRV QDDLDHPHTI TLLEGMKAKA PEGVNLMYER GCDWTEEIET KYGELGDARA WEYELLHRKV DSGEKADKAN ALKLAKLADV IVAAVGENVM LCGENRDRKG LRLPGKQEQF VKELLATGKP VVLVMFGGRA QVVSGLAEQC AAVIQAWYPG EEGGNAVADI LYGKVSPSAK LSVSYPNTEV YEPLCYNCQA EKDPRVQWPF GYGLSYTTFE YQNLKVDSAA TTADQSINLS FEVKNTGQVA ADEIAQIYLS |

TABLE 1-continued

THE PRIMARY STRUCTURES OF C1 TO C12

```
                PTADDQQIRP IQLQGFARVS LNPGETKTVK VKLYTEQFGF
                YTNDGKRLWI VRPGSFIVKV GASSQDIRLQ QQVTLSGNLV
                SNPLKEFYFS KTSIE

C7 (SEQ ID NO: 7)   MAFITVNFMS EALMRTVTVH VVLPADKIAE PGMPEPKHTD
                FPALYLLHGV FGNQTDWALR TRVQRMAENS DLALIMPAGE
                NAFYLDQEAT HANYGDFVGR ELPEIMRRMF PLSPRREDCF
                IAGLSMGGYG ALRNGLKYHE TFSRIGAFSA ALVLDGIENR
                TNDSPLFIER RDYAEAIFGP LDKVAESDIN PLWIARRLVE
                SGTELPGLYL ACGTEDFLFE PNVRFRDEVR KLGCELTWDE
                GPYGHEWDFW NLQVEKFIDW LPLSESGTGI DSGNVGI

C8 (SEQ ID NO: 8)   MKRKNHISLA MAFLAIGLMG TTVAKAQSAQ PDFDDKYATE
                MVKAGTTAPD FKMKTPDGKT IQLSKYIKAR PKDKGKTVVL
                DFWASWCPDC RKDAPEVVRL YEKYRPYGIE FIGISMDTDV
                EAWKKAIEQY GITYPQVSEL KKFKETDIAK AYGVKWIPSM
                VVVGPDGEVK LSTVLTYKVD KYLKELTTGK YAGPGKGEAV
                FIDGDHGRLK AIIQKPELQQ GEKCPMVIFC HGFSGRKDGP
                MFELIADTLQ AHGIASIRFD FNGHGESEGE FKDMTVPNEI
                EDAKKVVEYV RDLRYVSSLA IVGHSQGGVV AAMTAGQLSE
                ALGEPAFKAV ALMAPAAVLR DDAIRGNTMG KQYDPFDPGE
                YVELWGGLKL GGKYIRTAFS LPIYETAAKY QGPALVIHGN
                ADRVVPYTYG ERFHQIWPNS ELVIQEYFDH GFSQNLYRTT
                DIVSEYLIKQ LKK

C9 (SEQ ID NO: 9)   GKGETVFIDG DLGRLKALIQ KPALQQGEKC PMVIFCHGFS
                GTKDGPLFEL VADTLQAHGI ASIRFDFNGH GESEGEFKDM
                TVPNEIEDAK KVVEYVSDLR YVSSLAIVGH SQGGVVAAMT
                AGQLSEELGE SPFKAVVLMA PAAVLRDDAI RGSTMGKQYD
                PFDPGEYVEL WGGLKLGGQY IRTAFSLPIY ETAAKYQGPA
                LVIHGNADRV VPYTYGERFH QIWPKSELVI QEYFDHGFSQ
                NIYRTTDIVS EYLIKQLKSK

C10 (SEQ ID NO: 10) MGARVNAVMD EAVSGNKIVG AELIVYRHGD LVLRRTAGHF
                DREAGTPMIE NAIYRLASVT KPIVAATALA MIDKGLLRLD
                DLVSDHLDYF APLLDDGSPA PITIHHLLTH TAGLAYGYDD
                EAISTGLGPT DNDFRSNFTR IAKAPLLFAP GSGWNYSVAI
                DVLGAVLAAV HGGSLQDAVH AHITGPLGMD ETGFFVADLA
                RLAKPYADGA PEPTAMTDPQ SVIGEDGGSV VFSPSRIFSD
                KAFQSGGAGM AGTPENIAKF LETLRQGGGS VLRPDTVALA
                FSNRIGDLYR QDQGQRFGYF GAVIDDPVAA ESPSGAGTVN
                WGGVYGHSWL VDPTNAITIV SMSNTALEGC TGRYPKDLIR
                AVYDDLS

C11 (SEQ ID NO: 11) MTTLLLILLL ALALIAAAAW LFTVRTVRKV EAFLPPQGRF
                VEVPGARLHI VEKGEGRPLL LIHGLAGVLN HFTYGMVDEL
                AKHYRVIAVD RPGSGYSVRG AGASANLFDQ ADVMAALIDN
                LKLDRPVVVG HSLGGAVSLA LAQRHPQKVA ALALIAPLTH
                KPARISPAFD GLKIPSNWLR HALAWTLAVP VGLIKRDEIL
                AIVFGPEPVL EDFGTQGGGL LGVRPSHFIA ACADMNSELA
                QLLDMEKRYP AMQLPVGVFF GRGDLILDYR EQGEALASKV
                PGAELLLVDG GHMLPLTMVQ KSADFVRGVV ARA

C12 (SEQ ID NO: 12) MPIPDMAEFF TLAHFSDVHL PPVFGSGWRH WNAKRALGYM
                NWLRKRRRVH HGEVADKLLA DAAALRVDHI AITGDLINLG
                LPSEYEAAHA WLQSIGSPED VTVVPGNHDI YSSLHGDPGV
                ARWAEYMGGE NDTLAFPPFVR RVGPIAVVGL NSAVETPPFI
                ASGRLGAHQL EIAGEQLEAL GEKGIARVVM IHHPPLPDLA
                PPRRALSDAA HFAHLLERGN AELVIYGHNH QSRVDWLPSR
                TKPIPVVGVA SASAGVTHGD EPLASYNLFT FFKSDSGLRI
                RHVVRGIDAP NSPVRKISEA VLTPPP
```

Some of the genes possess notable features. The C1, C3, C8, and C9 genes have a TlpA-like ORF (thioredoxin-like open reading frame) at the 5' end of the sequence. Theoredoxin-like proteins are known to function in various cellular processes to reduce, oxidize, or isomerize thiol:disulfides. A partial sequence of a pullulanase is found in the opposite orientation of the C5 gene sequence. A sequence coding for ketopantoate reductase is located in opposite direction of the C9 gene.

TABLE 2

FAE genes and proteins characterization

| Clone Name | Gene Location (Insert Size) | Reference Sequence | % Identity to Ref Seq | Number of Residues (Includes tag) | SEQ ID NO | Recombinant Size (kDa) |
|---|---|---|---|---|---|---|
| Rum-C1 | 1811-2497 (687 bp) | ZP_01061020.1 Hydrolase of ⁻ Family | 45 | 229 | 1 | 25.2 |
| Rum-C2 | 587-1396 (810 bp) | ZP_01061020.1 Hydrolase of ⁻ Family | 45 | 269 | 2 | 29.7 |
| Rum-C3 | 663-1343 (681 bp) | ZP_01061020.1 Hydrolase of ⁻ Family | 46 | 381 | 3 | 41.9 |
| Rum6-C4 | 112-831 (720 bp) | AAF70241 Feruloyl Esterase A | 41 | 246 | 4 | 27.1 |
| Rum-C5 | 60-1001 (942 bp) | ZP_01122099.1 probable lipase/esterase | 32 | 416 | 5 | 45 |
| Rum-C6 | 2871-3827 (957 bp) | YP_169760.1 hypothetical protein lipase/esterase | 34 | 422 | 6 | 45.6 |
| Rum-C7 | 447-1277 (831 bp) | ZP_01777732 putative esterase | 48 | 277 | 7 | 32.3 |
| Rum-C8 | 1849-3207 (1359 bp) | ZP_01061020.1 Hydrolase of ⁻ Family | 47 | 382 | 8 | 41.9 |
| Rum-C9 | 66-1403 (1338 bp) | ZP_01061020.1 Hydrolase of ⁻ Family | 47 | 383 | 9 | 41.9 |
| Mul-C10 | 181-1281 (1101 bp) | ZP_01421329 Beta-lactamase | 44 | 367 | 10 | 39.7 |
| Mul-C11 | 116-1057 (942 bp) | YP_583166 alpha/beta hydrolase | 54 | 322 | 11 | 34.7 |
| Mul-C12 | 1495-2412 (918 bp) | YP_578455 metallophosphoesterase | 43 | 319 | 12 | 34.8 |

The gene sequences range from 681 bp (C3) to 1359 bp (C8). The upper range is the result of the additional Tlp-like protein sequence at the 5' end, which was not used for cloning. The structural gene sequences vary from 681 (C3) to 1101 (C10) bp. In the gene-vector construction, the signal sequence was deleted before ligation to the Trx-tag sequence in the pET32b vector.

Phylogenetic tree analysis of relatedness with known FAE's suggests that the novel FAE's fall within three major clusters. C5 and C6 in cluster 1 have a common node, so do C7 and C11, C9 and C10 in cluster 2, as well as C3 and C8 in cluster 3. This relationship is also reflected in the sequence homology. For example, C5 and C6 sequences share 84% identity and 90% similarity. In terms of calculated distance values, C2 and C5 show lesser degree of divergence than the others. C1, C3, C7, C8, C9, C11, and C12 have greater divergence, while C1, C2, and C10 are in the intermediate range. All these results provide further support on the diverse and novel nature of the genes.

The C1, C2, C4, and C7 genes containing the signal sequence cloned into pET29b, were expressed in BL21 as soluble proteins. The C3, C5, C6, C8, C9, C10, C11, C12, were constructed in fusion with the 342 bp TrxA tag into pET32b resulting in the production of soluble protein. The sizes of the recombinant enzymes range from 25.2 (C1) to 45.6 kD (C6). The enzyme preparations obtained by Ni-Sepharose affinity chromatography of the cell extracts were >90% pure by SDS-PAGE. The final stocks of the enzyme preps had concentrations ranging from 1.7 mg to 7.3 mg per ml.

The recombinant FAE's have varying pH optima in neutral and alkaline range, and retained substantial activities from pH 7.0 to 9.0, using ground corn fiber as the substrate. C4, C5, C6, and C7 remained quite active at pH 6, while C6 showed considerable activity at pH 5. The FAE's operated at various temperature optima. C4, C5, C7, and C10 showed optimum activity at 40° C. C6 was most active at 50° C. C6 and C7 maintained considerable activity at 60° C. C8 and C9 were cold-active enzymes, showing optimum activity below ambient temperature. C4 had the highest activity in releasing FA from corn fiber, followed by C6 and C5, at pH 7.0, 37° C., 2 hr incubation. The observed effects of pH and temperature may not be exclusively on the enzyme, as alkaline pH and high temperature could affect the fiber and effectively increase or decrease substrate accessibility to enzymatic degradation.

The choice of vector in which the DNA of interest is operatively linked depends directly, as is well known in the art, on the functional properties desired, e.g., replication, protein expression, and the host cell to be transformed, these being limitations inherent in the art of constructing recombinant DNA molecules. The vector desirably includes a prokaryotic replicon, i.e., a DNA sequence having the ability to direct autonomous replication and maintenance of the recombinant DNA molecule extra-chromosomally when introduced into a prokaryotic host cell, such as a bacterial host cell. Such replicons are well known in the art. In addition, preferred embodiments that include a prokaryotic replicon also include a gene whose expression confers a selective advantage, such as a drug resistance, to the bacterial host cell when introduced into those transformed cells. Typical bacterial drug resistance genes are those that confer resistance to ampicillin or tetracycline, among other selective agents. The neomycin phosphotransferase gene has the advantage that it is expressed in eukaryotic as well as prokaryotic cells.

Those vectors that include a prokaryotic replicon also typically include convenient restriction sites for insertion of a recombinant DNA molecule of the present invention. Typical of such vector plasmids are pUC8, pUC9, pBR322, and pBR329 available from BioRad Laboratories (Richmond, Calif.) and pPL, pK and K223 available from Pharmacia (Piscataway, N.J.), and pBLUESCRIPT and pBS available from Stratagene (La Jolla, Calif.). A vector of the present invention may also be a Lambda phage vector including those Lambda vectors described in Molecular Cloning: A Laboratory Manual, Second Edition, Maniatis et al., Eds., Cold Spring Harbor Press (1989) and the Lambda ZAP vectors available from Stratagene (La Jolla, Calif.). Other exemplary vectors include pCMU [Nilsson et al. (1989) Cell 58:707]. Other appropriate vectors may also be synthesized, according to known methods; for example, vectors pCMU/Kb and pCMUII used in various applications herein are modifications of pCMUIV (Nilson et al., supra). Typical expression vectors capable of expressing a recombinant nucleic acid sequence in plant cells and capable of directing stable integration within the host plant cell include vectors derived from the tumor-inducing (Ti) plasmid of *Agrobacterium tumefaciens* described by Rogers et al. (1987) Meth. in Enzymol. 153:253-277, and several other expression vector systems known to fraction in plants. See for example, Verma et al., No. WO87/0055 1; Cocking and Davey (1987) Science 236: 1259-1262.

A transgenic plant can be produced by any means known to the art, including but not limited to *Agrobacterium tumefaciens*-mediated DNA transfer, preferably with a disarmed T-DNA vector, electroporation, direct DNA transfer, and particle bombardment (See Davey et al. (1989) Plant Mol. Biol. 13:275; Walden and Schell (1990) Eur J. Biochem. 192:563; Joersbo and Burnstedt (1991) Physiol. Plant. 81:256; Potrykus (1991) Annu. Rev. Plant Physiol. Plant Mol Biol. 42:205; Gasser and Fraley (1989) Science 244:1293; Leemans (1993) Bio/Technology. 11:522; Beck et al. (1993) Bio/Technology. 11:1524; Koziel et al. (1993) Bio/Technology. 11:194; and Vasil et al. (1993) Bio/Technology. 11:1533). Techniques are well-known to the art for the introduction of DNA into monocots as well as dicots, as are the techniques for culturing such plant tissues and regenerating those tissues.

Feruloyl esterase of the invention can be used to improve the ferulic acid availability in a food or feed. Ferulic acid has antioxidant activity, and can be made available through feruloyl esterase treatment of a foodstuff. Agricultural grains may be treated with feruloyl esterase, advantageously in combination with xylanase, and be consumed to serve as a ferulic acid based antioxidant supplement, especially in humans. In addition to plant-derived solid food or feed treated with feruloyl esterase or the combination of feruloyl esterase and xylanase, liquids (beverages, e.g.) can also comprise feruloyl esterase (or feruloyl esterase and xylanase) treated material or soluble products thereof. If the beverage contains the solid foodstuff or feedstuff, enzymes are added at a ratio of from about 1 to 200 units of enzyme per kg, desirably from about 10 to about 50 U/kg of esterase and for xylanase, from about 100 to about 10,000 U/kg dry weight of plant-derived material in the liquid foodstuff or beverage. A feruloyl esterase described herein, desirably in combination with a cellulase and/or xylanase, for example that from *Orpinomyces* PC-2, can also be used in the pulping and paper recycling industries.

The ratio of the esterase to solids is from about 0.1 to about 200 U/kg dry weight, desirably from about 1 to about 100 U/kg, and advantageously from about 10 to about 50 U/kg. The feruloyl esterases and mixtures thereof or combination of feruloyl esterase and xylanase can be formulated as dry materials or as liquid concentrates for subsequent use in combination with a source of plant-derived non-starch polysaccharide or poorly digestible plant fiber material to be treated. Such a formulation can be freeze-dried in the case of a dry material or it can be a liquid concentrate.feruloyl esterase and xylanase to improve nutrition.

The feruloyl esterases of the invention may be used to improve the digestibility or energy source availability for humans, poultry (e.g., chickens, turkeys, ducks, geese, and other fowl), swine, sheep, cattle, horse, goats, fish (including but not limited to salmon, catfish, tilapia and trout) and shellfish, especially shrimp, and other farmed animals. Food or feed ingredients which are improved by treatment with feruloyl esterase include, without limitation, wheat, rye, barley, oats, corn, rice, soybean, millet, sorghum, grasses, legumes and other pasture and forage plants. Fresh or dry feed or food components can be treated with a liquid comprising the ferulic acid esterase so that the particles of the food or feed are coated with the enzymes. Similarly, wet or dry enzyme compositions can be added to a liquid food or feed composition so that the ratio of enzymes to dry weight or plant material is as taught herein.

Feruloyl esterase proteins are also characterized by at least a portion having from at least about 50% amino acid sequence identity with an amino acid sequence as given in SEQ ID NO's:1-12. Sequences included in this invention are also those amino acid sequences which are 50, 60, 70, 75, 80, 85, 90, 95 to 100%, identical to the amino acid sequences encoded by the ferulic acid esterases coding sequence of SEQ ID NO's: 1-12 and corresponding to or identifying encoded proteins which exhibit feruloyl esterase activity. In comparisons of protein or nucleic acid sequences, gaps go introduced into either query or reference sequence to optimize alignment are treated as mismatches. It is well-known in the biological arts that certain amino acid substitutions may be made in protein sequences without affecting the function of the protein. Generally, conservative amino acid substitutions or substitutions of similar amino acids are tolerated without affecting protein function. Similar amino acids can be those that are similar in size and/or charge properties, for example, aspartate and glutamate, and isoleucine and valine, are both pairs of similar amino acids. Similarity between amino acid pairs has been assessed in the art in a number of ways. For example, Dayhoff et al. (1978) in Atlas of protein Sequence and Structure, Volume 5, Supplement 3, Chapter 22, pp. 345-352, which is incorporated by reference herein provides frequency tables for amino acid substitutions which can be employed as a measure of amino acid similarity. Dayhoff et al.'s frequency tables are based on comparisons of amino acid sequences for proteins having the same fraction from a variety of evolutionarily different sources. A further embodiment of the invention is the use of the FAE's for crosslink degradation releasing fibers from lignocellulosic biomass without further action of other enzymes to obtain intact oligosaccharides and polysaccharides for feed, food, and industrial applications. This process also finds utility in soluble fiber release from brewer's grain, beet pulp, corn steeping, residual food processing, agricultural residue and waste. Oligosaccharides and controlled conversion of polysaccharides to oligosaccharides can perform as prebiotics for both human and animals, and serve to enhance gut and intestinal health.

Additional applications for the feruloyl esterase enzymes of the present invention, include producing ferulic acid from wheat bran or agricultural byproducts, pretreating biomass to for downstream waste or sewer treatment, using the enzyme to treat grasses, grains, maize bran, generation of fiber in situ, waste residue of rice bran oil or other plant materials which are used in the pulp and paper industry, wet milling, feed processing—including improving the digestibility of animal feed, as a food additive. The Biotransformation of the ferulic acid to vanillin may also be accomplished by microbial transformation using Generally Recognized as Safe Microorganisms. The present invention further provides methods for improved pulping of plant material or recycled fiber materials, wherein the improvement comprises the step of adding a feruloyl acid esterases of the invention to the pulping mixture and incubating under conditions allowing enzymatic action of the esterase on the non-starch polysaccharides in the mixture. If further hydrolysis of polysaccharides is required, the substrate specificity and other catalytic properties imparted by each esterase allows for greater control and processing in the products formed.

Cloning of the genes of the invention into recombinant hosts provides a selection of feruloyl esterases that may be uniquely tailored for targeted applications including the applications set forth above. Standard techniques for cloning, DNA isolation, amplification and purification, for enzymatic reactions involving DNA ligase, DNA polymerase, restriction endonucleases and the like, and various separation techniques are those known and commonly employed by those skilled in the art, standard techniques are described in Sambrook et al. (1989) *Molecular Cloning*, Second Edition, Cold Spring Harbor Laboratory, Plainview, N.Y.; Maniatis et al. (1982) *Molecular Cloning*, Cold Spring Harbor Laboratory, Plainview, N.Y.; Wu (ed.) (1993) *Meth. Enzymol.* 218, Part I; Wu (ed.) (1979) *Meth. Enzymol.* 68; Wu et al. (Eds.) (1983) *Meth. Enzymol.* 100 and 101; Grossman and Moldave (Eds.) *Meth. Enzymol.* 65; Miller (ed.) (1972) *Experiments in Molecular Genetics*, Cold Spring Harbor Laboratory, Cold Spring Harbor, N.Y.; Old and Primrose (1981) *Principles, of Gene Manipulation*, University of California Press, Berkeley; Schleif and Wensink (1982) *Practical Methods in Molecular Biology*; Glover (ed.) (1985) *DNA Cloning Vol. I and II*, IRL Press, Oxford, UK; Haines and Higgins (Eds.) (1985) *Nucleic Acid Hybridization*, IRL Press, Oxford, UK; and Setlow and Hollaender (1979) *Genetic Engineering: Principles and Methods*, Vols. 1-4, Plenum Press, New York.

An additional embodiment of the invention is a novel method for rapid screening and isolation of genes of interest from complex genomes of any bioresources including microbial, plant or animal. The method includes the formulation and use of a substrate gel assay plate, and an enrichment process by serial dilutions progressive to isolate the target gene from a DNA library, wherein the DNA library may be genomic or cDNA. Initial extraction of the genomic or cDNA libraries proceed by methods known to one of skill in the art. The substrate gel contains a combination of a detecting/expression solution and a gelling growth medium. The base components of the detection/expression solution contain (1) a buffer at a suitable pH; (2) a non-ionic detergent at concentration 1-3% (v/v), preferably 1-2% (v/v); (3) a suitable substrate for detecting expression of the target gene. The growth medium contains a low melt agarose at 1-3% (w/v), preferably 1.5% (w/v) melted and mixed into a suitable nutrient broth such as Luria Bertani (LB) or other suitable growth medium. Types of substrates may include chromogenic, fluorogenic, soluble or insoluble dye-crosslinked substrates, which enable the detection of the targeted enzyme reaction product to be quickly visualized and/or measured spectroscopically. The inclusion of antibiotics and expression inducers depends on the type of libraries, which can be constructed based on *Escherichia coli*, bacteriophages, phagemid, and other expression vectors.

The approach departs from conventional methods used for screening genomic or cDNA libraries conferring the advantages of: (1) screening library of clones in split pools; (2) localizing and intensifying positive signals on a substrate gel plate; and (3) progressive enrichment and isolation of positive clones using serial dilutions with high-throughput robotic capabilities. Rapid isolation of a diverse repertoire of candidate genes for tailor-making enzymes and routes leading to new bioprocesses and bioproducts are achieved. This invention may be packaged into commercial kits to provide a convenient and universal tool for gene discovery.

Methods

Genomic Library Construction and Activity Screening

Genomic DNA was extracted and purified from the microflora of cow's rumen or other environmental samples, followed by partial digestion separately with EcoRI and ApoI. The digests were combined and selected for fragments of sizes from 1 to 8 kb by agarose gel electrophoresis. The fragments were purified and ligated into X-ZAP-II predigested EcoRI/CIAP-treated vector. The recombinant vector mixture was packaged using Gigapack III packaging extract, and the resulting primary library was amplified to a titer of $10^{10}$ pfu/ml based on blue-white color selection. This amplified library was subjected to enzyme activity screening as described in [0027] to [0039].

Subcloning of FAE Genes

The identified gene sequence was amplified from the genomic DNA by PCR and cloned in pET29b and pET32b, both containing a C-terminal His-tag. The pET32b vector contains additionally a Trx-tag fusion at the N-terminal end. The N-terminal end His-tag between the Trx-tag and the C-terminal His-tag in the vector was deleted during the gene-vector construction. The final construction was verified by DNA sequencing before used for transformation.

Expression and Purification

The recombinant gene-vector construct was used to transform *E. coli* BL21(DE3). Positive transformants were selected by halo formation growing on ethyl ferulate agar plates. Positive clones were further confirmed by liquid assay of FAE activity using p-nitrophenyl ferulate as the substrate. A single positive transformant was used to inoculate 2 ml LB and incubated overnight at 37° C. at 225 rpm. A 2 ml overnight culture was transferred to 200 ml fresh LB, and incubated for 3 hr to an $OD_{600\ nm}$ of 0.7. Induction of protein expression was initiated by the addition of 0.1 mM of IPTG, and incubation was allowed to proceed for 4 more hr at 30° C. Thereafter, the cells were pelleted and lyzed using 8 ml of primary amine-free Bug-Buster reagent. The extracted protein was purified by Ni Sepharose affinity chromatography, using 20 mM sodium phosphate, 0.5M NaCl, 20 mM imidazole, pH 7.4 binding buffer, and the same buffer containing 500 mM imidazole as the elution buffer. Collected 1-ml fractions were analyzed for purity by SDS-PAGE. Combined active fractions were buffered exchanged into 20 mM sodium phosphate buffer, pH 7.4 with 10% glycerol, and concentrated by ultrafiltration.

Electrophoresis

The purified and concentrated enzyme was run on bis-tris gels using 50 mM MOPS running buffer, pH 7.7 at 200 V constant for 50 min, and stained with Coomassie G-250. For molecular weight determination, the bands were analyzed against protein standards by image analysis software (Alpha Innotech, CA).

Enzyme Activity Measurements

Enzyme activity in the transformants was detected by halo formation by plating the colonies on ethyl ferulate agar plates. The enzyme activity was further confirmed by liquid assay using p-nitrophenyl ferulate as the substrate. The purified FAE's were characterized for biochemical properties using corn fiber as the substrate. Enzyme activity was expressed as μg ferulic acid released per 100 mg corn fiber at pH 7.0 and 37° C.

Determination of pH and Temperature Optima

For pH optimum, the reaction mixture was incubated for 2 h at 37° C., using corn fiber as the substrate at varying pH using a citric acid/sodium phosphate universal buffer. Parallel controls were conducted for all pH points without the enzyme. For temperature optimum, the reaction was incubated for 2 hr in universal buffer, pH 7.0. Parallel controls were conducted for all temperature points without the enzyme.

HPLC Analysis of Ferulic Acid

Ferulic acid released from enzymatic hydrolysis of corn fiber was measured by HPLC. The analysis was performed using a SphereClone 5μ ODS column with $H_2O$/HCOOH/$CH_3CN$ (7:1:2) as the solvent, at a flow rate of 0.2 ml/min at ambient temperature. The effluent was monitored with a UV detector at 300 nm. Ferulic acid was applied as external standard for calculation.

Method of Gene Discovery

I. Making Substrate Gel Assay Plate

A substrate gel is formulated and set in a 96 well microtiter plate as an assay plate for screening and detecting the target gene expression. The DNA library is split into small pools (sub-libraries) for growth and amplification of the cell populations in each of the wells in the assay plate. Cells grown in each well are in direct contact with the substrate gel with enhanced permeability and diffusion to maximize cell-substrate interactions and reactions. The substrate gel set in each well enables the localization of the reaction products confined within the well area with enhanced detection sensitivity.

Substrate Gel Assay Plate

In one tube, low-melt agarose at 1.5% (w/v) is melted into LB or any suitable growth medium and cooled to 50° C. In a separate tube, buffer, detergent, antibiotic, inducer, and substrate are added to the growth medium and equilibrated to 50° C. An example would include 50 mM sodium phosphate buffer, pH 6.5, 1.67% (v/v) detergent Triton X-100, 50 μg/ml antibiotic ampicillin, 2 mM expression inducer IPTG, and 2 mM substrate p-nitrophenyl ferulate in DMSO added to LB medium to a final volume of 25 ml and equilibrated to 50° C. After equilibrating both tubes, one containing the agarose mix and the other substrate mix, to 50° C., the two tubes were combined and poured in 10-ml aliquots into a reservoir. Using an 8-channel pipetter fitted with 1.2 ml tips, the combined mix was dispensed to 96-well, half-area microtiter plates (polystyrene, flat-bottom from Greiner) at 50 μl per well. A volume of 50 ml was sufficient for making 9 assay plates. After hardening, the assay plates are used immediately, or can be stored at 4° C. for several weeks. The gelling growth medium must contain 1.67% low-melt agarose. The substrate tube should at least contain the base components (1) a buffer at a suitable pH, (2) a non-ionic detergent, (3) a suitable substrate for detecting expression of the target gene. Types of substrates may include chromogenic, fluorogenic, soluble or insoluble dye-crosslinked substrates, which enable the detection of the targeted enzyme reaction product to be quickly visualized and/or measured spectroscopically by a plate reader. The inclusion of antibiotics and inducers depends on the type of libraries, which can be constructed based on *Escherichia coli*, bacteriophages, phagemid, and suitable expression vectors known to one of skill in the art.

II. Application of Substrate Gel Plates for Screening DNA Libraries

In a general scheme, 5 μl of an overnight culture of each DNA library pool (see below) is transferred from culture plates into individual wells of the premade substrate gel assay plate. The assay plates are covered with a porous membrane and incubated and monitored for the formation of reaction products due to expression of the target gene. Wells showing product formation indicate active pools, which are subjected for enrichment to isolate the positive clone.

A Protocol Example for Screening a Phagemid Library

An aliquot of a phagemid library containing ~1×105 cfu (cell formation units) is diluted into 80 ml of LB ampicillin (50 μg/ml), and 0.1 ml of the diluted phagemid is dispensed per well into eight 96-well, flat-bottomed microtiter plates. Each well therefore contains 1×105 cfu divided by 800, equivalent to ~125 cfu per well. Each individual well represents a sub-library (sub-populations) of the original DNA library. The plates are covered with a permeable membrane and incubated overnight at 850 rpm and 37° C. in a microtiter plate incubator shaker. These culture plates are used to inoculate the pre-made substrate gel assay plates, and afterwards stored at 4° C. as the master plate containing sub-libraries.

The overnight cultures from individual wells of the culture plates are transferred in 5 μl volume onto the wells of the assay plates. The assay plate was covered with a permeable membrane and incubated without shaking at 30° C. or 37° C. overnight. Typically, assay plate wells containing active pools (that is, containing a positive clone in the cell population) would produce the reaction product detectable within 8 hours at 37° C.

III. Enrichment for Isolation of an Active Clone from a Positive Pool

Positive Wells of the assay plate are identified and referred to the corresponding sub-libraries in the master plates. A serial dilution scheme is developed to enable quick enrichment and isolation of the active clone(s) from the cell population in the positive pool, as described in the following protocol.

On a 96-well microtiter plate, each column represents an individual sampling from a single well of the master sub-library growth plate. Each row is a serial dilution of that sampling starting from row A and continuing to row H (8 dilutions). Usually, 2 to 4 samplings of the master well were done and each sampling was serially diluted.

An aliquot of 2.5 μl of the sub-library is added to 122.5 μl of growth medium in row A, resulting in a 1:5 dilution. Next, 25 μl from row A is diluted in 100 μl growth medium in row B, resulting in a further 1:5 dilution. This is continued to row H to a final dilution of ~8×105. The plate was covered with a porous membrane and shaken overnight at 850 rpm and 37° C. The next day, 5 μl of the overnight culture in each well is assayed using the premade substrate gel assay plates as described above The serial dilution growth plates are stored at 4° C., as the master dilution culture plates. The most dilute well showing positive detection is sampled, serially diluted, and assayed again in the same manner as described above. Eventually, all the wells in the assay plate will become positive, indicating a homogeneous population of the positive clone.

What is claimed:

1. A feruloyl esterase composition comprising a feruloyl esterase selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, and mixtures thereof; and a plant derived composition containing ferulic acid crosslinks.

2. The feruloyl esterase composition of claim 1, wherein the plant derived composition is selected from the group consisting of agricultural food, agricultural waste, animal feed and paper.

3. The feruloyl esterase composition of claim 2, wherein the agricultural food and waste is selected from the group consisting of grasses, grains, maize, bran, corn steeping and vegetable pulp.

4. A method for increasing free ferulic acid content of a plant-derived composition, said method comprising the step of contacting a plant-derived composition with a feruloyl esterase wherein said feruloyl esterase comprises a feruloyl esterase selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12 and mixtures thereof.

5. The method of claim 4, wherein the plant derived composition is selected from the group consisting of agricultural food, agricultural waste, animal feed, paper, municipal waste and industrial waste.

6. The method of claim 5, wherein the agricultural food and waste is selected from the group consisting of grasses, grains, maize, bran, corn steeping and vegetable pulp.

* * * * *